US006596777B1

(12) United States Patent
Schiraldi et al.

(10) Patent No.: US 6,596,777 B1
(45) Date of Patent: *Jul. 22, 2003

(54) MOISTURE CONTAINING COMPOSITIONS THAT ARE SPREADABLE ONTO AND ADHERABLE TO BIOMEMBRANES

(75) Inventors: Michael T. Schiraldi, Wilmington, NC (US); Katherine M. Burnett, Basking Ridge, NJ (US)

(73) Assignee: McNeil-PPC, Inc., Skillman, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/865,169

(22) Filed: May 29, 1997

(51) Int. Cl.$^7$ ................................. A61K 47/32
(52) U.S. Cl. ................................... 514/772.4
(58) Field of Search ............... 424/436, 424, 424/772.6, 777; 514/967

(56) References Cited

U.S. PATENT DOCUMENTS

| 2,798,053 A | 7/1957 | Brown |
| 3,074,852 A | 1/1963 | Mayron |
| 3,330,729 A | 7/1967 | Johnson |

(List continued on next page.)

FOREIGN PATENT DOCUMENTS

| AT | 84 418 B | 8/1993 |
| DE | 41 39 883 A1 | 6/1993 |
| EP | 0 297 828 | 1/1989 |
| EP | 0 371 421 A2 | 6/1990 |
| EP | 0 431 719 | 6/1991 |
| EP | 0 524 587 | 1/1993 |
| GB | 1090421 | 11/1967 |
| GB | 1431092 | 4/1976 |
| WO | 89/06964 | 8/1989 |
| WO | 90/02542 | 3/1990 |
| WO | WO 91/06283 A1 | 5/1991 |
| WO | WO 96/03973 | 2/1996 |
| WO | WO 96/10989 A1 | 4/1996 |

OTHER PUBLICATIONS

Database WPIL on Questel, week 9601, London: Derwent Publications Ltd, AN 96–010662, Class A 61 K, WO 95/31 178 A1 (Jansseen Pharm NV), abstract.
Database WPIL on Questel, week 9421, London: Derwent Publications Ltd., AN 94–167998, Class A 01 N, CA 21058 87 A (Britton et al.) abstract.

(List continued on next page.)

Primary Examiner—Thurman K. Page
Assistant Examiner—Charesse Evans

(57) ABSTRACT

This invention relates to compositions that are easily spreadable onto and adhesive to biomembranes. They contain and provide moisture to the biomembranes and do not readily flow off, i.e., leak from the biomembranes. Nor are they readily removed or washed from the biomembranes. Compositions that adhere to and are compatible with, in that they spread, and do not flow off and are not readily removed or washed from the biomembranes are deemed to be bioadhesive. Such compositions are particularly useful for maintaining biomembranes in a moist condition, for lubricating the biomembranes, and for providing a vehicle for containing and delivering medicaments, such as contraceptives, antifungals and antibacterials. The invention further relates to methods for making and methods of use of such compositions. The compositions of this invention are particularly useful for maintaining biomembranes in a moist condition, especially those that are susceptible to dryness, for lubricating the biomembranes and for providing a vehicle for containing and delivering medicaments, such as contraceptives, antifungals and antibacterials.

20 Claims, 2 Drawing Sheets

U.S. PATENT DOCUMENTS

| | | | |
|---|---|---|---|
| 4,188,373 A | | 2/1980 | Krezanowski |
| 4,226,848 A | | 10/1980 | Nagai |
| 4,261,969 A | * | 4/1981 | Heller .................... 424/433 |
| 4,304,591 A | * | 12/1981 | Mueller et al. ............ 424/436 |
| 4,615,697 A | | 10/1986 | Robinson |
| 5,225,196 A | * | 7/1993 | Robinson .................... 424/434 |
| 5,292,517 A | | 3/1994 | Chang |
| 5,385,729 A | * | 1/1995 | Prencipe et al. ......... 514/772.6 |
| 5,393,798 A | | 2/1995 | Weber |
| 5,474,768 A | * | 12/1995 | Robinson .................... 514/967 |
| 5,750,579 A | * | 5/1998 | Kamishita et al. ....... 514/772.6 |
| 5,840,744 A | * | 11/1998 | Borgman .................... 514/967 |
| 5,874,096 A | * | 2/1999 | Hazen ....................... 514/777 |

OTHER PUBLICATIONS

Database WPIL on Questel, week 9251, London: Derwent Publications Ltd., AN 92–418582, Class A 61 K, JP 4–312–521 A (Okkamoto Co., Ltd.) abstract.

Database WPIL on Questel, week 9230, London: Derwent Publications Ltd., AN 92–249830, Class A01 N, WO 92/10998 A1 (Bombart), Abstract.

Database WPIL on Questol, week 8917, London: Derwent Publication Ltd, AN 89–126027, Class A 61 K, JP 1–710823A (Rohto Pharmaceutical KK), abstract.

* cited by examiner

MOISTURE CONTAINING COMPOSITIONS THAT ARE SPREADABLE ONTO AND ADHERABLE TO BIOMEMBRANES

FIELD OF THE INVENTION

This invention relates to compositions that are easily spreadable onto and adhesive to biomembranes. They contain and provide moisture to the biomembranes and do not readily flow off, i.e., leak from, the biomembranes. Nor are they readily removed or washed from the biomembranes. Compositions that adhere to and are compatible with, in that they spread, and do not flow off and are not readily removed or washed from the biomembranes are deemed to be bioadhesive. Such compositions are particularly useful for maintaining biomembranes in a moist condition, for lubricating the biomembranes, and for providing a vehicle for containing and delivering medicaments, such as contraceptives, antifungals and antibacterials. The invention further relates to methods for making and methods of use of such compositions.

BACKGROUND OF THE INVENTION

Polymers which have been known in the past for use in bioadhesive compositions include insoluble polymers, dispersible polymers and soluble polymers, all with reference to their solubility in aqueous media. For purposes of the following discussion, both dispersible and insoluble polymers are meant to refer to polymers that are crosslinked to the extent that makes them insoluble in aqueous media. Soluble polymers are either not crosslinked or crosslinked to such a minor extent that they are entirely soluble in aqueous media. Thus, dispersible polymers are herein considered to have such limited solubility as to be essentially insoluble, despite the fact that, although they do not dramatically precipitate from solution, they may appear to be soluble. Such dispersible polymers reflect their insolubility by being capable of being separated from aqueous media by methods such as centrifugation or filtration.

Robinson, in U.S. Pat. No. 4,615,697 describes a controlled release treatment composition including a bioadhesive and an effective amount of treating agent, the bioadhesive comprising a water swellable, but insoluble, fibrous, i.e., particulate, crosslinked carboxy functional polymer.

U.S. Pat. No. 2,798,053 describes, for carboxyvinyl polymers, useful crosslinking agents that are not free of polyalkenyl polyethers, such as polyallyl sucrose or polyallylpentaerythritol containing an average of about three allyl groups per molecule, as in CARBOPOL 934.

The bioadhesives of U.S. Pat. No. 4,615,697 are water insoluble, in that they separate from the aqueous solution in which they are prepared. U.S. Pat. No. 3,074,852, U.S. Pat. No. 3,330,729 and U.S. Pat. No. 4,226,848 describe bioadhesives that contain water dispersible polymers having CARBOPOL 934, a polymer of acrylic acid that is crosslinked with polyallyl sucrose, the polymers being minimally crosslinked to so as to become sufficiently "water soluble" to provide a measurable viscosity at 0.2 weight % in water. However, it is apparent from its very limited solubility, that CARBOPOL 934 is considered to be water dispersible rather than water soluble.

Most recently, Robinson in U.S. Pat. No. 5,474,768 added to the formulation described in U.S. Pat. No. 4,615,697 a water dispersible, viscosity enhancing, agent consisting of a nonionic or anionic polymer, the anionic polymer having, for example, a plurality of carboxyl groups.

Potts et al, in U.S. Pat. No. 4,188,168 describes an aqueous topically administered ophthalmic composition, having a pH less than 5, containing N-(5-sulphamoyl-1,3,4-thiadiazol-2-yl)acetamide, otherwise known as acetolazolamide, and either: a) a preformed aqueous gel, or b) an aqueous gel-forming polymer capable of forming gel in-situ when applied topically. The in-situ gel is a "thermal gel" which is liquid at room temperature and gels at body temperature, having a sol-gel transition between 25–40° C. Examples are Pluronic or Tetronic polyoxyethylene polyoxypropylene copolymers, as are described in U.S. Pat. No. 4,188,373.

Chandrasekaran in WO 89/06964 describes a topical ophthalmic medicament delivery system, rapidly gellable on contact with the eye's tear fluid, containing: an aqueous suspension, of pH 3–6.5, osmotic pressure 10–400 mOsM, and viscosity 1000–30,000 cp, containing 0.1–6.5% of a lightly crosslinked carboxyl containing polymer that has a particle size <50 μm in equivalent spherical diameter.

Chang, in U.S. Pat. No. 5,292,517 describes a reversible gelling, erodable drug delivery composition that exhibits a change in solution viscosity in response to changes in pH. The composition contains an aqueous solution from 1–25% w/v At the polymer poly(methylvinylether/maleic acid) having a number average molecular weight from 20.000–100.000: and 0.005–50% w/v of a therapeutic or diagnostic pharmaceutical compound that is stable in the presence of the polymer. Exposure to higher physiological pH, as in the eve. causes the polymer to deprotonate and thereby unwind its polymeric chain. The polymeric chain, now occupying increased polymeric volume, has increased resistance to flow: thereby adhering to the tissue and providing sufficient time for the pharmaceutical compound to be biologically available.

U.S. Pat. No. 5,393,798 describes a hydrogel material comprised of copolymers of poly(alkylvinylether/maleic acid), containing a modifying group R selected from the group consisting of —NH—$(CH_2)_{1-5}$—CH=$CH_2$ and —NH—CO—NH—$CH_2$CH=$CH_2$, where the modifying group is substituted for one of the hydroxyl groups of a maleic acid moiety.

Previous products that employ polycarboxyl groups containing polymers attempt to achieve adhesion of the formulations to biomembranes and to prevent them from leaking from or washing off the biomembranes, depending for bioadhesion on hydrogen bonding of the carboxyl groups to the biomembranes, the source of the carboxyl groups being water insoluble, albeit water swellable polymers. Although crosslinking prevents the polymer from washing off or leaking from the biomembrane, it limits to a significant degree the availability of the hydrogen bonds of the carboxyl groups to interact with the carboxyl groups present on the biomembrane.

Therefore, it is an object of this invention to provide spreadable lubricious compositions, buffered to a bioacceptable pH, and having a pseudoplastic elastic modulus profile, the compositions being adhesive to biomembranes such as oral, vaginal and ophthalmic mucosa.

It is a further object of this invention to provide such spreadable lubricious compositions that also contain and provide moisture to the biomembranes, do not readily flow off, or leak from, the biomembranes, and are not readily removed or washed from the biomembranes.

It is yet another object of this invention to provide spreadable lubricious compositions that require much lower amounts of polyhydroxy compound when compared with known formulations, and yet provide enhanced lubricity.

It is still a further object of this invention to describe methods for making such compositions.

It is yet still a further object of this invention to describe methods of use of such compositions.

SUMMARY OF THE INVENTION

Figure 1:
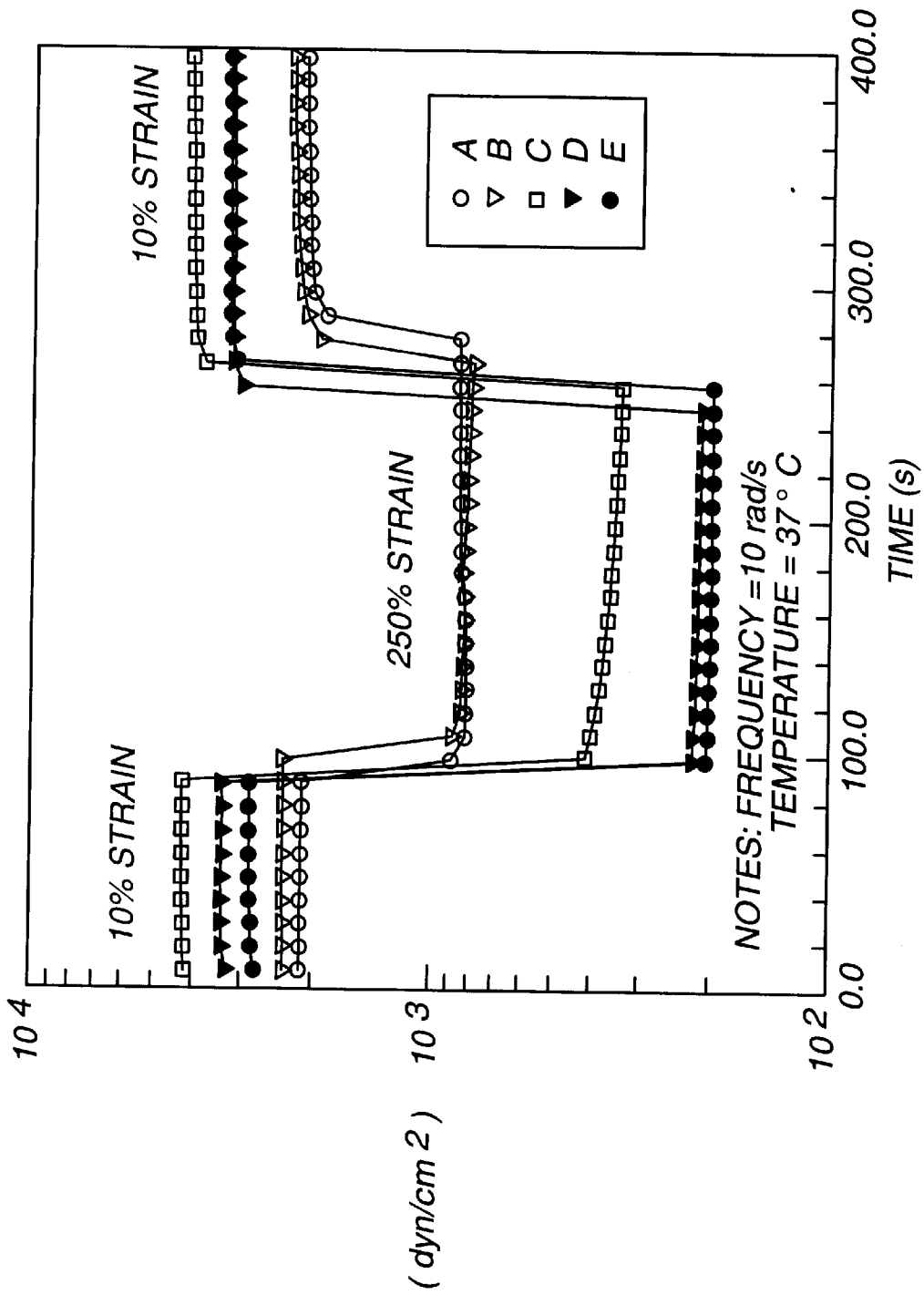
FIG. 1 is a graph representing a plot for several formulations of the elastic modulus as a function of time.
Figure 2:
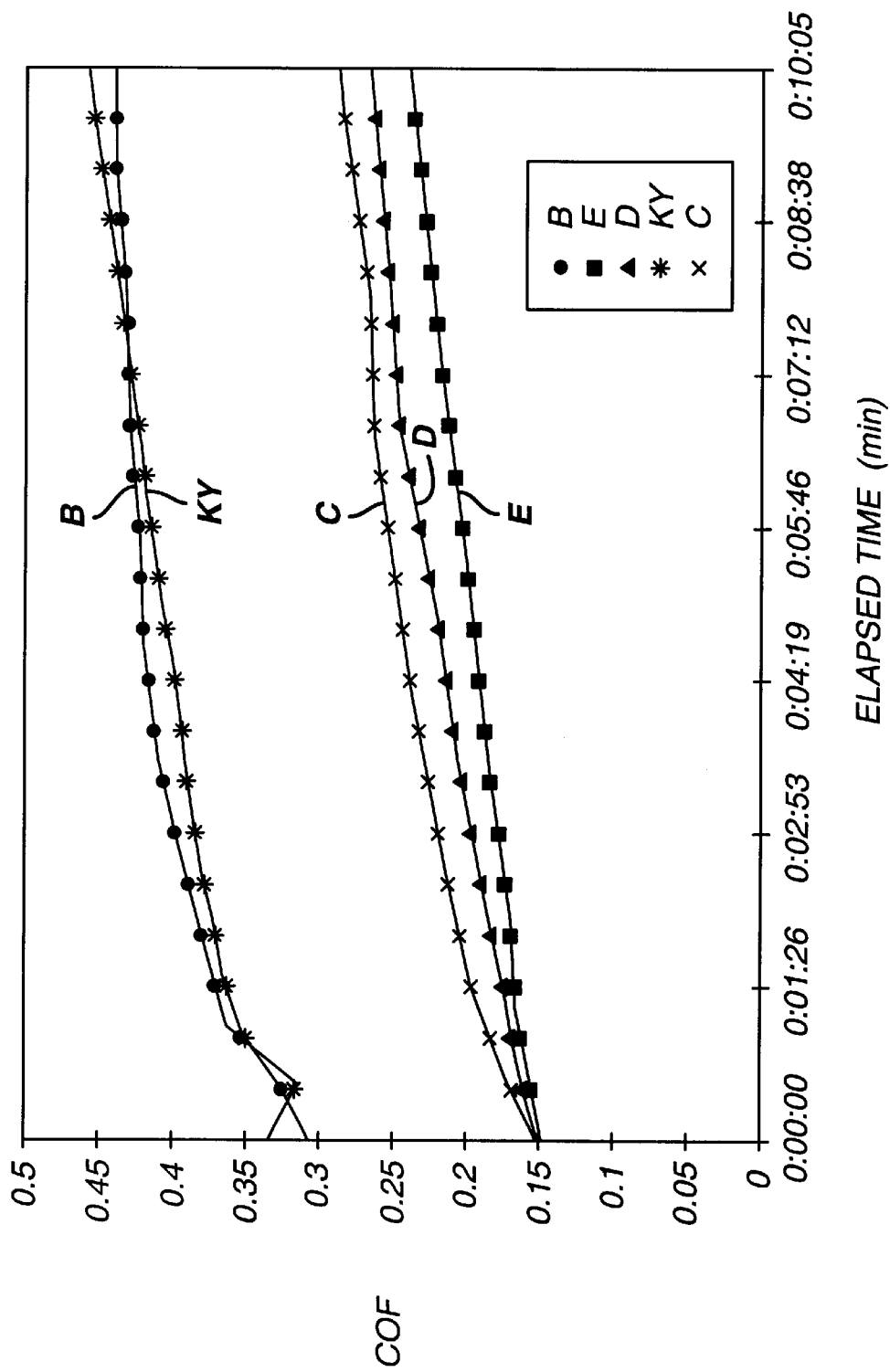
FIG. 2 is a graph representing the coefficient of friction as a function of time for several formulations.

This invention relates to spreadable lubricious compositions, buffered to a bioacceptable pH, and having a pseudoplastic elastic modulus profile. The compositions of this invention are adhesive to biomembranes such as oral, vaginal and ophthalmic mucosa contain and provide moisture to the biomembranes, do not readily flow off, i.e., leak from, the biomembranes, and are not readily removed or washed from the biomembranes.

The composition of this invention preferably contain: a crosslinked polymer, a water soluble polymer, a polyhydroxy compound, water and a base in an amount sufficient to neutralize the composition to a pH that is biologically acceptable to the biomembrane to which the composition will be applied. The compositions preferably contain a cation in an amount that enhances adhesion of the composition to the biomembrane, but less than that which will cause precipitation of the water soluble polymer. This cation is preferably selected from the group of alkali metals, alkaline earth metals and amine cations. Most preferably, this cation is calcium. The compositions of this invention also preferably require 5% or less of polyhydroxy compound, and yield surprisingly enhanced lubricity, when compared to commercial formulations that contain 10 to 25% polyhydroxy compound. The invention additionally describes methods for making and methods of use of such compositions.

In addition to a crosslinked polymer which preferably contains carboxyl groups, this invention should contain a water soluble carboxyl group-containing polymer, the carboxyl groups of which are fully available for bioadhesion. The matrix of the crosslinked polymer holds the water soluble polymer and water within the compositions of this invention and thereby hold substantially prevent them from leaking from or washing off the biomembrane. Additionally, bioadhesion is further enhanced by the presence of calcium ion. The calcium ions form bridges between the carboxyl groups of the soluble and insoluble polymers and the carboxyl groups of the biomembrane. The amount of calcium ion present should be sufficient in order to assist in forming bridges, or crosslinks, between the carboxyl groups of the soluble and insoluble polymers and the carboxyl groups of the biomemebrane, but not so large as to precipitate the polymers as well as reduce their ability to swell and to imbibe water.

The compositions of this invention are particularly useful for maintaining biomembranes in a moist condition especially those that are susceptible to dryness, for lubricating the biomembranes and for providing a vehicle for containing and delivering medicaments, such as contraceptives, antifungals and antibacterials.

DETAILED DESCRIPTION OF THE INVENTION

Preferably, the compositions of this invention contain the following components: a crosslinked polymer containing carboxyl groups, a water soluble polymer, a polyhydroxy compound, water and a base in an amount sufficient to neutralize the composition to a pH that is biologically acceptable to the biomembrane to which the composition will be applied.

The crosslinked polymers present in the compositions of this invention physically associate with themselves so as to create a viscous network. This network can accommodate water soluble polymer and water within itself, and yet can associate with biomembranes. The crossliriked polymer is preferably a water-dispersible or water soluble polymer and is preferably chosen from polyalkylacrylic acids such as of methylacrylic acid and ethylacrylic acid, crosspolymers of vinylacrylates and acrylic acid (RHEOLATE 5000), sodium carboxymethyl cellulose (AQUASORB), vinylalkylether maleic anhydride copolymers and their hydrolysis products such as copolyvinylmethylether maleic anhydride (STABLESE) and copolyvinylethylether maleic anhydride, polymers of maleic acid, maleic anhydride, fumaric acid, crotonic acid, angelic acid, tiglic acid, cinnamic acid, coumaric acid, umbellic acid. α-benzylacrylic acid, α-butylacrylic acid, α-phenylacrylic acid, α-cyclohexylacrylic acid, sodium carboxymethyl cellulose ethers, and combinations thereof and the like. Monomers that may be copolymerized with the carboxy functional monomers are: alkyl acrylates such as hexyl acrylate, butylmethacrylate, methyl crotonate, hydroxyethyimethacrylate, hydroxypropylmethacrylate and tetraethylene glycol monoacrylate: acrylamides such as methylacrylamide, acrylamide, N-methylacrylamide, N-butylmethylacrylamide and N,N-dimethylacrylamide: and styrene.

Most preferably, the crosslinking agent used in the compositions of this invention to create the crosslinked polymer is 1,9-decadiene, used with vinylmethylether maleic anhydride copolymer. Other examples of crosslinking agents that may be preferably used with this and other polymers and copolymers are polyalkenyl ethers, divinyl glycol, trialiyl isocyanate, divinyl benzene, N,N-diallyl acrylamide, 3,4dihydroxy-1,5-hexadiene, 2.5-dimethyl-1,5-hexadiene, polyallyl sucrose, polyalylypentaervthritol, ethylene and polvethylene glycol diacrylates, trimethyloipropane triacrylate and trimethyioipropane trimethacrylate.

Relatively low concentrations, most preferably about 1.4%, of the crosslinked water insoluble polymer are needed, although it can range from about 0.5% to about 2%. The concentration of water insoluble polymer may range from about 0.1% to about 5%, and preferably from about 0.8% to about 1.8%.

Additionally, rheological modifiers may be added to the composition, such as magnesium silicate (Laponite), organically modified clay (Bentone) and magnesium aluminum silicate, as well as other materials known to those of skill in the art.

The water soluble polymer of the compositions of this invention is preferably chosen from noncrosslinked polymers such as polycarboxylic acids, or from potential polycarboxylic acids on hydrolysis such as polyanhydrides, and combinations thereof, that are neutralized for example with sodium hydroxide or coneutralized for example with sodium and calcium hydroxides. Examples of these are sodium carboxymethyl cellulose, sodium-calcium polycarboxymethyl cellulose, sodium polyacrylates, sodium-calcium polyacrylates (Rohm-Pharma) and vinylmethylether maleic acid copolymers or vinylethylether maleic anhydride copolymers, wherein the latter may be any or all of the free acid form (Gantrez S-95), the sodium neutralized form, or preferably the sodium-calcium coneutralized form (Gantrez 955). Other examples of water soluble polymers that may be used are polyethylene oxides, polyvinylpyrrolidone homopolymers and polyvinylpyrrolidone vinylacrylate copolymers. Preferably, More preferably, Most preferably, These polymers may complex with carboxyl groups, such as polyethylene oxides and polyvinyl pyrrolidone, and may be used if they lend some additional esthetic or functional property. However, they should be used in concentrations that are sufficiently low so as not to interfere with the ability of the carboxyl groups to adhere to biomembranes.

Fairly low concentrations of the water soluble polymer are needed in the compositions of this invention in order to provide function. The concentration of water soluble polymer may range from about 0.1% to about 25%, and preferably from about 0.2% to about 2%, most preferably, it should be present in an amount of about 0.5%.

Water can be an important component of the compositions of this invention in compositions intended to provide moisture to a biomembrane. Water, in the compositions of this invention, maintains the moist condition of the biomembrane and contributes greatly to the lubricity of the compositions. The concentration of water may range from about 30% to about 98%, and preferably from about 86% to about 96%. However, if another active ingredient were present, the formulation should he adjusted so as to accommodate the presence the additional active ingredient, which may entail reducing the level of water accordingly.

The polyhydroxy compound component contained in the compositions of this invention functions as a humectant and/or lubricant. It may also aid in product processing, preservation and stability. The polyhydroxy compound may be chosen, for example, from materials such as glycerin, propylene glycol, sorbitol and combinations thereof. Other examples of polyhydroxy compounds that may be used are hyaluronic acid and polyethylene glycols. Preferably, the polyhydroxy compound is glycerin.

The concentration of polyhydroxy compound may range from about 0.5% to about 25%, and preferably from about 1% to about 5%. In comparison, the prior art compositions such KY Lubricating Jelly, KY PLUS and REPLENS contain between 10 and 20% by weight of the composition. It has unexpectedly been found that the compositions of this invention, by containing such low concentrations of polyhydroxy compound, are even more lubricious than those containing higher concentrations of polyhydroxy compound.

The compositions of this invention may contain additional ingredients which provide other characteristics to the formulations for use on or in the body, such as emulsifiers including surfactants, lubricants and emollients, and preservatives.

Lubricants and emollients are primarily useful in reducing irritation due to frictional abrasion between biomembranes. Examples of lubricants and emollients are mineral oil, lanolin, glycerol monostearate, glyceryl caprylate, hydrogenated vegetable oil, castor oil, cholesterol and petrolatum. The concentration of lubricant may range from about 0.5% to about 10%, and preferably from about 1% to about 5%.

Emulsifiers are primarily useful to keep lubricants and emollients suspended, without causing them to settle out of suspension, thereby preserving physical stability of the emulsion. Examples of emulsifiers are hydrogenated palm glyceride and hydrogenated castor oil although any emulsifier known to those of ordinary skill in the art may be utilized. The concentration of emulsifier may range from about 0.1% to about 2%, and preferably from about 0.2% to about 1% by weight of the composition.

Preservatives may be added to the formulations according to this invention as fungistatic agents to inhibit the growth of molds, yeasts and/or bacteria in the formulation after production. Examples t)f preservatives are methyl paraben, propyl paraben, sorbic acid. chlorhexidine gluconate and mixtures of such products. The concentration of preservative may range from about 0.01% to about 2.0%, and preferably from about 0.025% to about 0.5%.

A bioacceptable pH is preferably maintained by creating a balance between the insoluble polymers, soluble polymers, e.g., the polycarboxylic acid or anhydride, and an acid, e.g., hydrochloric acid, or a base, e.g., sodium and/or calcium hydroxide. More preferably, the compositions of this invention should contain a base. Other bases that may be used, for example, may include ammonium hydroxide, potassium hydroxide, sodium carbonate, sodium bicarbonate and combinations of these and those already mentioned. For vaginal use the pH is preferably that which is compatible with vaginal tissue, i.e., less than 7, and more preferably approximately pH 4, to maintain the appropriate vaginal flora and discourage the growth of undesirable bacteria, yeasts, molds and viruses. The bioacceptable pH of such formulations may range from about 5.5 to about 2.7. The pH of normal vaginal mucus is 4.6 or less. For ophthalmic use, the pH should be in the range of from about 7.3 to about 7.5. For use in the oral cavity, the pH should be in the range from about 4 to about 8, the lower end of the pH range reflecting the possible need to treat the teeth and gums with hydrofluoric acid.

Preferably, the compositions of this invention should contain a small amount of calcium ion in order to enhance the adhesion of the formulation to the mucosa, provided that the calcium ion concentration does not exceed that which will cause precipitation of the polymer. Thus, for example, if the composition of this invention contains a water soluble polymer having salts of calcium and sodium due to the adjustment of the pH with calcium and sodium hydroxides, the amount of calcium in, for example a 1% w/w solution of Gantrez 955 will be about 0.00075 mole equivalent of calcium hydroxide. This amount is well below that needed to precipitate the polymer, if the water soluble polymer contains only the sodium salt as is usual for example with commercially available polyacrylic acid, it is preferred that calcium hydroxide be added, the ratio of sodium hydroxide to calcium hydroxide required being dependent on the type of polyacrylic acid or polyacrylate. For example, when a 5% w/w solution of polymethylvinylether maleic anhydride copolymer (Gantrez AN) is hydrolyzed to its free acid form, its pH is then raised by adding base containing no more than 0.7 mole equivalents of calcium hydroxide so that the polymer does not precipitate. The preferred range of calcium hydroxide is between about 0.0001 and about 0.0025 mole equivalents, with the most preferred range being about 0.00035 to about 0.0015 mole equivalents.

Calcium ion in the compositions of this invention may be present in soluble forms other than calcium hydroxide, e.g., calcium chloride, calcium bromide, calcium nitrate and calcium acetate, as long as it is in forms and concentrations that promote adherence to biomembranes without causing precipitation of the water soluble polymer.

The compositions of this invention may, in addition to their use as moisturizers, be used to deliver medicament to biomembranes. For example, the compositions of this invention may contain active ingredients useful as medicaments for vaginal use, such as antifungals, antibacterials, antivirals, antiirritants, anesthetics, analgesics, antiinflammatories, spermicides, vitamins and medicaments to treat or prevent sexually transmitted diseases. Examples of antifungals are miconazole, ketoconazole, itraconazole, metronidazole, clotrimazole, butaconazole, terconazole, saperconazole, econazole, troconozole and other imidazole compounds, or other antifungal agents known to those of ordinary skill in the art. An example of a vitamin is Vitamin E. Examples of spermicides are nonoxynol-9, octoxynol-9 and p-methanylphenyl polyoxyethylene (8,8) ether and the like. An example of an analgesic or antiirritant is phenazopyridine. Examples of drugs to treat or prevent sexually transmitted diseases are nonoxynol-9, octoxynol-9, p-menthanylphenyl polyoxyethylene (8,8) ether and sulfonated polysaccharides. Examples of antibacterials are povidone iodine, triplennamine hydrochloride and chlorhexidine gluconate. Of course, other active ingredients may be used in the compositions of this invention that are well-known to those of skill in the art.

The compositions of this invention may also be used to deliver ophthalmic medicaments, such as antifungals, antibacterials, antivirals, antiirritants, anesthetics, analgesics, antiinflammatories, drugs to treat glaucoma and sympathatomimetics. Examples of drugs to treat glaucoma are dipivefrin hydrochloride, timolol maleate, acetylcholine chloride ephedrin hydrochloride, naphazoline hydrochloride, phenylephrine, tetrahydrazoline and pilocarpine hydrochloride. An example of a sympathatomimetic is epinephrine.

Likewise, medicaments for use in the oral cavity may be delivered using the compositions of this invention, such as antifungals, antibacterials, antivirals, antiirritants, anesthetics, analgesics, steroids, antiinflammatories, sodium chloride, tissue healing substances, tissue regeneration agents and dental remineralization agents. One example of an antifungal is nystatin chlortrimazole. Examples of local anesthetics are benzocaine, butacaine, eugenol, phenol, menthol, clove oil and lidocaine. Examples of steroids are hydrocortisone and triamcinolone acetonide, Examples of antibacterials are povidone iodine and chlorhexidine gluconate. An example of a dental remineralization agent is sodium fluoride.

EXAMPLES

The following Examples set forth illustrations of preferred compositions according to this invention and methods of preparing such compositions. These examples are illustrative only and should not be interpreted to restrict or limit the scope of the invention in any way.

Example 1

The following Formulation D, is intended for vaginal use. It is a clear composition which contains the following ingredients (concentrations in weight percent):

1.4% Stablese 06, a polyvinylmethylether maleic anhydride copolymer crosslinked with 1,9-decadiene 0.5% Gantrez MS 955, polyvinylmethylether maleic anhydride copolymer, coneutralized with calcium and sodium hydroxides 2.5% Glycerin, USP 99%

0.2% Methyl paraben 0.5% Sorbic acid 95.3% Water, USP 0.053% Sodium hydroxide (30%) to buffer to pH 4

Formulation was made by first placing water in a main vessel. Gantrez MS 955 is added to the water, while heating to 75° C.; and is mixed until uniform. At 70–75° C. Stablese 06 is added and the composition mixed until uniform, adjusting agitation to facilitate good turnover. In a second vessel, glycerin is heated to 75° C., followed by the addition of methyl paraben and sorbic acid. With high agitation, the glycerin mixture from the second vessel is added to the water mixture in the main vessel. After mixing until uniform, sufficient sodium hydroxide is added to bring the pH to 4. Mixing is continued at a lower level of agitation for two hours. The resulting product is a lubricious composition which is easily spreadable and bioadhesives.

Example 2

Formulation E, for vaginal use, is a creamy composition which contains (concentrations in weight percent) the following ingredients:

1.4% Stablese 06, a polyvinylmethylether maleic anhydride copolymer crosslinked with 1,9-decadiene 0.5% Gantrez MS 955, polyvinylmethylether maleic anhydride copolymer, coneutralized with calcium and sodium hydroxides 2.5% Glycerin, USP 99%

0.02% Methyl paraben 0.05% Sorbic acid 1.5% Mineral oil 0.5% Hydrogenated palm oil glyceride 93.3% Water, USP 0.053% Sodium hydroxide (30%) to buffer to pH 4

Formulation E was made as follows: In a main vessel, Gantrez MS 955 is added to water, while heating to 75° C.; and the composition is mixed until uniform. At 70–750° C., Stablese 06 is added and mixed until uniform, adjusting agitation to facilitate good turnover. In a second vessel, glycerin is heated to 75° C., followed by the addition of methyl paraben and sorbic acid. In a third vessel, mineral oil is heated to 75° C., and hydrogenated palm oil glyceride is added and mixed until clear. The contents of this vessel is gradually added to that of the second vessel. With high agitation, the glycerin mixture from the second vessel is added to the water mixture in the main vessel. After mixing until uniform, sufficient sodium hydroxide is added to bring the pH to 4. Mixing is continued at a lower level of agitation for two hours. The resultant composition is a spreadable cream for use with biomembranes.

Example 3

In the formulation of this example, a clear composition is made using the same components and concentrations as those of Example 1, except that Gantrez MS 955 is present in the amount of 0.25% and water is present in the amount of 95.5% (concentrations in weight percent).

Example 4

In the formulation of this example, a creamy composition is made using the same components and concentrations as Example 2, except that Gantrez MS 955 is present in the amount of 0.25% and water is present in the amount of 95.5% (concentrations in weight percent).

Examples 5–10

The following examples have the same components as those of Examples 1 and 3, containing, 0.5% and 0.25%

Gantrez 955 respectively, except that the amount of gyvcerin was varied from 5 to 15% and the amount of water was reduced accordingly. Concentrations are in percent by weight.

| Example | 5 | 6 | 7 | 8 | 9 | 10 |
|---|---|---|---|---|---|---|
| Water | 92.8 | 87.8 | 82.8 | 93.1 | 88.1 | 83.1 |
| Glycerin | 5.0 | 10.0 | 15.0 | 5.0 | 10.0 | 15.0 |
| Stablese 06 | 1.4 | 1.4 | 1.4 | 1.4 | 1.4 | 1.4 |
| Gantrez MS 955 | 0.5 | 0.5 | 0.5 | 0.5 | 0.5 | 0.5 |
| Methyl Paraben | 0.2 | 0.2 | 0.2 | 0.2 | 0.2 | 0.2 |
| 30% Sodium Hydroxide | 0.53 | 0.53 | 0.53 | 0.53 | 0.53 | 0.53 |

Examples 11–13

Propylene glycol was used instead of glycerin in these examples, whereas the Gantrez MS 955 in Examples 11 and 12 has the same components and their concentrations, other than glycerin, as those of Examples 1 and 3 respectively, and Example 13 has the same components and their concentrations, other than glycerin, as those of Examples 2.

| Example | 11 | 12 | 13 |
|---|---|---|---|
| Water | 95.5 | 95.3 | 93.3 |
| Propylene Glycol | 2.5 | 2.5 | 2.5 |
| Stablese 06 | 1.4 | 1.4 | 1.4 |
| Gantrez MS 955 | 2.5 | 0.5 | 0.5 |
| Methyl Paraben | 0.2 | 0.2 | 0.2 |
| Mineral Oil | — | 1.5 | — |
| Hydrogenated Palm Glyceride | 0.5 | — | — |
| 30% Sodium Hydroxide | 0.53 | 0.53 | 0.53 |

Example 14

A formulation for vaginal use in accordance with the compositions of this invention was made as follows: Deionized water, 935 (rams, was added to glycerin, 50 grams, and heated to 50–55° C., while stirring. Stablese 06, 2.5 grams, was added until complete dissolution was achieved. The solution was cooled to room temperature. Gantrez AN-119 copolymer was added and vigorously stirred for 30 minutes until complete dissolution was achieved. Calcium hydroxide, 0.278 grams, was then added, followed by sufficient 30% sodium hydroxide to attain a pH of about 4.

Example 15

A formulation for vaginal use in accordance with the compositions of this invention was made as follows: Deionized water, 935 grams, was added to glycerin, 10 grams, and heated to 50–55° C., while stirring. Stablese 06, 2.5 grams, was added until complete dissolution was achieved. A polyacrylate, Rhoplex AC-33, was added to this solution. Calcium hydroxide. 0.278 grams, was then added, followed by sufficient 30% sodium hydroxide to attain a pH of about 4.

Examples 16–17

Formulations according to this invention for use as vaginal moisturizers were made as follows: Preparation of stock solution: Deionized water, 1820 grams, was added to glycerin, 150 grams, and heated to 45–50° C. CARBOPOL 934P was added to this vigorously stirred solution until complete dispersion of gels and clumps was achieved.

Preparation of formulation of Example 16: NaCMC (sodium carboxymethylcellulose),7MXF, 5 grams, was added to 995 grams of the stock solution, with stirring, until it was completely dissolved. The pH was adjusted to 4.6 with 30% NaOH.

Preparation of formulation of Example 17: Gantrez MS 955, 5 grams, was added to 995 grams of the stock solution, with stirring, until it was completely dissolved. The pH was adjusted to 4.75 with 30% NaOH.

Examples 18–19

Formulations of compositions in accordance with this invention for vaginal use were made as follows:

Preparation of stock solution: Deionized water, 1870 grams, was added to glycerin, 100 grams, and heated to 45–50° C. AQUASORB 307 was added to this vigorously stirred solution until complete dispersion was achieved.

Preparation of formulation of Example 18: NaCMC, 7MXF, 5 grams, was added to 995 grams of the stock solution, with stirring, until it was completely dissolved. The pH was adjusted to 3.25 with 30% HCl.

Preparation of formulation of Example 19: Gantrez MS 955, 5 grams, was added to 995 grams of the stock solution, with stirring, until it was completely dissolved. The pH was adjusted to 4.5 with 30% HCl.

Example 20

A formulation of a composition in accordance with this invention for vaginal use was made as follows:

Glycerin, 50 grams, was added to deionized water, 935 grams, and heated to 45–50° C., while stirring. Stablese 06, 10 grams, was added to this vigorously stirred solution until complete dissolution was achieved. Gantrez S-95, 5 grams, was added to this solution. The pH was adjusted to 3.8 by adding 30% sodium hydroxide.

Example 21

The following formulation for ophthalmic use, to provide moisture to dry eyes, was made as follows: Deionized water, 490 grams, was added to glycerin, 6.25 grams, and heated to 50–55° C while stirring. Stablese 06, 2.5 grams, was added to this solution, followed by the addition of Gantrez 955, 1.25 grams. After complete dissolution of the polymers, the pH was adjusted to 7.3–7.5 by adding 30% sodium hydroxide.

Example 22

The following example of a vaginal formulation containing Vitamin E as a medicament is: water, 93.2%; glycerin. 2.5%; Stableze 06 (copolymer of methylvinylether and maleic anhydride, crosslinked with 1,9decadiene). 1.4%; Gantrez MS 955 (calcium and sodium neutralized copolymer of methylvinylether and maleic anhydride), 0.5%; mineral oil, 1.5%: Myverol 18-04 (hydrogenated palm glyceride), 0.5%; methyl paraben. 0.2%; sorbic acid. 0.5%; vitamin E acetate, 0.1%; sodium hydroxide, 0.53%.

The flow, spreading and lubricity characteristics of the compositions were tested using both in vitro and in vivo test methods, which are described below.

In Vitro Measurements

Viscoelastic measurements were performed on samples "as is", i.e., they did not require being concentrated. A Rheometrics RDA2 Rheometer that is capable of measuring low torques in the range 0.2 to gm-cm was used. Good flow and spreading requires a low value for the elastic modulus during application to the biomembrane by the user: and a high elastic modulus after the formulation is applied to minimize flow and leakage from the biomembrane during use. Elastic modulus is calculated using the following equation:

Elastic Modulus=Loss Modulus/Loss Tangent

This equation dictates a requirement, for this invention, that the Loss Tangent should have a low value during application and a high value during use. For formulations of this invention. the flow viscosity changes from high to low and back to high, before application, during application and during use, respectively, whereas the viscous modulus changes very little. Loss Tangent values, as a function of shear rate, show that compositions of this invention having the properties of remaining in position on the biomembrane, e.g., vaginal mucosa. during use, also have a higher loss modulus than compositions that do leak off the biomembrane.

Graph 1 is a plot, for several formulations. A, B, C, D and E, at 37° C., of the elastic modulus, in dynes/cm$^2$, as function of time, in seconds, when the strain is increased from 10% to 250% and then decreased to 10%. Formulation A contains: water, about 15–25% glycerin. about 1–5% total of hydroxyethylcellulose, sodium carboxymethylcellulose and polyvinylpyrrolidone, a pH buffering agent, and preservatives. Formulation B contains: water, about 15–25% glycerin, about 1–5% total of hydroxyethylcellulose, sodium carboxymethylcellulose and polyvinylpyrrolidone, mineral oil, an emulsifier, a pH buffering agent and preservatives. Formulation C is REPLENS vaginal moisturizer, which contains a crosslinked water insoluble, water swellable polymer and is available commercially from Columbia Laboratories of New York, N.Y. Formulations D and E are as set forth in Examples 1 and 2, respectively, above. Formulations C, D and E all exhibit large decreases in elastic modulus with increase in strain, the decreases being greater than 2000 dynes/cm$^2$, whereas compositions A and B exhibited decreases in elastic modulus well below 2000 dynes/cm$^2$. The decrease in elastic modulus reflects the amount of pseudoplasticity exhibited by each composition and, in turn, is correlated with the ease with which the composition spreads and adheres to mucosa. Thus, composition C, D and E spread easily and adhered to and were retained on vaginal and buccal mucosa: whereas compositions A and B did not spread nor adhere easily and were susceptible to easy removal and leaking off the mucosal surface. Surprisingly, the compositions of this invention, D and E, performed as well as composition C, which contained a cross-linked water swellable, water insoluble polymer.

Coefficient of friction measurements were made using a Friction Evaluation Device which moves a cylindrical probe, with preset load and speed values, over the surface to be measured. The frictional drag of the surface imparts a torque to the cylindrical probe. The probe contains a force gauge transducer that translates the torque into a force. The probe was covered with a lambskin condom to simulate the use conditions of the substrate being tested. here the biomembrane.

Graph 2 shows the coefficient of friction as a function of time, in minutes, for the formulations B, C, D, E and F, wherein B, C, D and E are those described above, and formulation F being: water, about 15–25% glycerin, about, 1–5% hydroxyethyl cellulose, a pH buffering agent and preservatives. The lowest coefficients of friction were exhibited by compositions C, D and E. These results correlate well with consumer preference tests that show C, D and E to he the most lubricious of the several formulations. Surprisingly, the compositions of this invention, D and E, performed as well as composition C, which contained a cross-linked water swellable, water insoluble polymer.

In Vivo Measurements

Cheek Test—An in vivo test for spreading and adhesion to biomembranes, called the "cheek test", is done by attempting to spread about one gram of the composition under test, with the tip of a finger onto the inside buccal surface of the mouth. Successful formulations. such as D and E of this invention, spread easily and stay put. Poor formulations for this purpose tend to ball up and not adhere, so that even quite viscous samples of such formulations are released or roll off the biomembranes.

What is claimed is:

1. A lubricious composition capable of application to a mammalian biomembrane consisting essentially of:
    a) polyvinylmethylether maleic anhydride cross-linked with 1,9-decadiene;
    b) polyvinylmethylether maleic anhydride coneutralized with calcium hydroxide, sodium hydroxide or a combination thereof;
    c) a polyhydroxy compound selected from the group consisting of glycerin and propylene glycol; and
    d) water.

2. A composition according to claim 1 wherein said polyhydroxy compound is present in the amount of from about 1% to about 5% by weight.

3. A composition according to claim 1 wherein said composition further comprises from about 0.0001 to about 0.0025 mole equivalents of calcium ions.

4. A composition according to claim 3 wherein the amount of base is sufficient to bring the pH of the composition within the range of about 2.7 to about 5.5, for us in the vagina.

5. A composition according to claim 1 wherein the composition further comprises a medicament for vaginal use selected from the group consisting of antifungals, antibacterials, antivirals, antiirritants, anesthetics, analgesedics, antiinflammatories and spermicides, vitamins and medicaments to treat or prevent sexually transmitted diseases.

6. A composition according to claim 3 wherein the amount of base is sufficient to bring the pH of the composition within the range of about 7.0 to about 7.5 suitable for ophthalmic use.

7. A composition according to claim 3 wherein the amount of base is sufficient to bring the pH of the composition within the ranges of about 6 to about 8, for us in the oral cavity.

8. A composition according to claim 7 wherein said composition further comprises a medicament for oral us selected from the group consisting of antifungals, antibacterials, antivirals, antiirritants, anesthetics, analgesics, antiinflammatories, tissue healing substances, tissue regeneration agents and dental remineralization agents.

9. A lubricious composition capable of application to a mammalian biomembrane consisting essentially of:
    a) a crosslinked polymer, containing carboxylic acid groups or groups that may be hydrolysed to form carboxylic acid groups, said polymer being selected from the group consisting of: crosslinked polyacrylic acid, polyvinylacrylic acid and polyalkylacrylic acids; crosspolymers of acrylated and acrylic acid; copolymers of acrylic acid and allylsucrose; copolymers of carboxy functional monomers with alkyl acrylates, alkyl acrylamides and styrene; hydroxyalkylcelluloses, sodium carboxyalkyl celluloses, calcium caboxyalkyl celluloses, and sodium carboxymethyl cellulose ethers; polymers of maleic acid, maleic anhydride, fumaric acid, crotonic acid, angelic acid, tiglic acid, cinnamic acid, coumaric acid, umbellic acid, α-benzylacrylic acid, α-butylacrylic acid, α-phenylacrylic acid, α-cyclohexylacrylic acid, vinylalkylether maleic acids, vinylalkylether maleic anhydrides; and combinations thereof;

b) from about 0.1% to about 25% of a water soluble, noncrosslinked polymer, containing carboxylic acid groups;

c) from about 0.5% to about 25% of a polyhydroxy compound, and d) from about 30% to about 98% water;

wherein said composition has an elastic modulus which decreases less than 2000 dynes/cm$^2$ when subjected to strain that increases from 10% to 250% and then decreases again to 10%.

10. A composition according to claim 9 wherein said polyhydroxy compound is present in the amount of from about 1% to about 5% by weight.

11. A composition according to claim 9 wherein said composition further comprises from about 0.0001 to about 0.0025 mole equivalents of calcium ions.

12. A composition according to claim 9 wherein said polyhydroxy compound is selected from the group consisting of glycerin, propylene glycol, sorbitol, hyaluronic acid, polyethylene glycols, propylene glycols and combinations thereof.

13. A composition according to claim 9 wherein the composition further comprises a base.

14. A composition according to claim 13 wherein said base is selected from the group consisting of sodium hydroxide, sodium bicarbonate, sodium carbonate, calcium hydroxide, ammonium hydroxide, potassium hydroxide, potassium hydroxide, potassium bicarbonate, potassium carbonate and combinations thereof.

15. A composition according to claim 13 wherein the amount of base is sufficient to bring the pH of the composition within the range of about 2.7 to about 5.5, for us in the vagina.

16. A composition according to claim 15 wherein the composition further comprises a medicament for vaginal us selected from the group consisting of antifungals, antibacterials, antivirals, antiirritants, anesthetics, analgesics, antiinflammatories and spermicides, vitamins and medicaments to treat or prevent sexually transmitted diseases.

17. A composition according to claim 13 wherein the amount of base is sufficient to bring the pH of the composition within the range of about 7.0 to about 7.5 suitable for aphthalmic use.

18. A composition according to claim 17 wherein said composition further comprises a medicament for ophthalmic use selected from the group consisting of antifungals, antibacterials, antivirals, antiirritants, anesthetics analgesics, steroids, antiinflammatories, drugs to treat glaucomas and sympathatomimetics.

19. A composition according to claim 13 wherein the amount of base is sufficient to bring the pH of the composition within the ranges of about 6 to 8, for use in the oral cavity.

20. A composition according to claim 19 wherein said composition further comprises a medicament for oral use selected from the group consisting of antifungals, antibacterials, antivirals, antiirritants, anesthetics, analgesics, antiinflammatories, tissue healing substances, tissue regeneration agents and dental remineralization agents.

* * * * *